United States Patent [19]

Chang et al.

[11] Patent Number: 5,552,286

[45] Date of Patent: Sep. 3, 1996

[54] HYBRIDOMA CELL LINES AND THEIR MONOCLONAL ANTIBODIES TO HUMAN PLURIPOTENT GRANULOCYTE COLONY STIMULATING FACTOR

[75] Inventors: David Chang, Thousand Oaks; Bruce Altrock, Newbury Park, both of Calif.

[73] Assignee: Kirin-Amgen, Inc., Thousand Oaks, Calif.

[21] Appl. No.: 382,942

[22] Filed: Jan. 31, 1995

Related U.S. Application Data

[63] Continuation of Ser. No. 243,055, May 16, 1994, abandoned, which is a continuation of Ser. No. 445,118, Nov. 30, 1989, abandoned, which is a continuation of Ser. No. 201,386, May 31, 1988, abandoned, which is a continuation of Ser. No. 806,755, Dec. 9, 1985, abandoned.

[51] Int. Cl.$^6$ .................. G01N 33/53; G01N 33/577; C12N 5/12; C07K 16/22
[52] U.S. Cl. .................. 435/7.2; 435/240.27; 435/172.2; 435/70.21; 436/537; 436/548; 530/388.23; 530/388.7; 530/388.1
[58] Field of Search .................. 435/240.27, 172.2, 435/70.21, 7.1, 7.2; 530/388.23, 388.7, 388.1; 436/548, 537

[56] References Cited

U.S. PATENT DOCUMENTS

| | | | |
|---|---|---|---|
| 4,504,586 | 3/1985 | Nicolson | 436/518 |
| 4,558,005 | 12/1985 | Goldwasser et al. | 436/548 |
| 4,558,006 | 12/1985 | Egrie | 436/548 |
| 4,810,643 | 3/1989 | Souza | 435/68 |
| 4,833,127 | 5/1989 | Ono et al. | 514/21 |
| 4,999,291 | 3/1991 | Souza | 435/69.1 |

FOREIGN PATENT DOCUMENTS

| | | |
|---|---|---|
| 0225583 | 6/1987 | European Pat. Off. . |
| 2092159 | 8/1982 | United Kingdom . |
| 8303678 | 10/1983 | WIPO . |

OTHER PUBLICATIONS

Begley, et al., Exp. Hematol., 13, 956–962 (1985).
Burgess, et al., Int. J. Cancer, 26, 647 (1980).
Burgess, et al., J. Biol. Chem., 252, 1998–2003 (1977).
Das, et al., Blood, 58, 630–641 (1981).
Fojo, et al., Biochemistry, 17, 3109–3116 (1978).
Metcalf, Int. J. Cancer, 25, 225 (1980).
Metcalf, Science, 229, 16–22 (1985).
Metcalf, et al., J. Cell. Physiol., 116, 198–206 (1983).
Metcalf, et al., Leukemia Research, 9, No. 5, pp. 521–527 (1985).
Moore, J. Cell Physiol. Supp. 1, 53–64 (1982).
Mortstyn, et al., J. Cell Physiol., 109, 133–142 (1981).
Nicola, Methods in Enzymology, 116, 600–619 (1985).
Nicola, et al., Genes and Cancer, pp. 591–610 (1984).
Nicola, et al., J. Biol. Chem., 258, 9017 (1983).
Nicola, et al., PNAS (USA), 81, 3765–3769 (1984).
Okabe, et al., J. Cell. Physiol., 110, 43–49 (1982).
Okabe, et al., JNCI, 69, 1235–1243 (1982).
Platzer, et al., Haematology and Blood Transfusion in Modern Trends in Human Leukemia VI, 29, 418, 422 (1985).
Ruppert, et al., Exp. Hematol., 11, 154–161 (1983).
Tsuneoka, et al., Cell Structure and Function, 9, 67–81 (1984).
Waheed, et al., Blood, 60, 238–244 (1982).
Welte, et al., J. Cell. Biochem., Supp. 9A, 116 (1985).
Welte, et al., "Leukemia: Recent Advances in Biology and Treatment," UCLA Symposia on Molecular and Cellular Biology, Gale, et al., eds., New Series, 28, 339–347 (1985).
Wang, F. F. et al., J. Cell. Biochem., 21:263–275, 1983.
De Lamarter, J. F. et al, Embo, 4(10):2575–2581, 1985.
Souza, L., Blood, 66(5):102, Aug. 21, 1985, abstract.
Maurer, P. H. et al, Methods in Enzymology, vol. 70:49–70, 1980.
Nicola, et al., Blood, 54, 614–627 (1979).
Nicola, et al., Nature, 314, 625–628 (1985).
Tsuchiya, et al., Proc. Natl. Acad. Sci. (USA), 83, 7633–7637 (1986).
Welte, et al., Proc. Natl. Acad. Sci. (USA), 82, 1526–1530 (1985).
Lopez, et al., J. Immunol., vol. 131, No. 6, (1983), pp. 2983–2988.

*Primary Examiner*—Lila Feisee
*Assistant Examiner*—Susan A. Loring
*Attorney, Agent, or Firm*—Marshall, O'Toole, Gerstein, Murray & Borun

[57] ABSTRACT

Murine-derived hybridoma tumor cell lines and monoclonal anti-human pluripotent Granulocyte Colony Stimulating Factor antibody substances produced by these cell lines. Use of said monoclonal antibody substances, alone or in combination, in immunological procedures for isolation of human pluripotent Granulocyte Colony Stimulating Factor and for quantitative detection of human pluripotent Granulocyte Colony Stimulating Factor in fluid samples.

4 Claims, No Drawings

HYBRIDOMA CELL LINES AND THEIR MONOCLONAL ANTIBODIES TO HUMAN PLURIPOTENT GRANULOCYTE COLONY STIMULATING FACTOR

This application is a continuation of application Ser. No. 08/243,055, filed May 16, 1994, now abandoned, which is a continuation of application Ser. No. 07/445,118, filed Nov. 30, 1989, now abandoned, which is a continuation of application Ser. No. 07/201,386, filed May 31, 1988, now abandoned, which is a continuation of application Ser. No. 06/806,755, filed Dec. 9, 1985, now abandoned.

BACKGROUND OF THE INVENTION

The present invention relates generally to materials and methods for use in immunological procedures for isolation and quantitative detection of hematopoietic growth factors from biological fluids. Specifically, the invention relates to monoclonal antibodies produced by novel hybridoma cell lines (as exemplified by A.T.C.C. HB-8957, A.T.C.C. HB-8958, A.T.C.C. HB-8959, A.T.C.C. HB-8960, A.T.C.C. HB-8961 and A.T.C.C. HB-8962) which are specifically reactive with hematopoietic growth factors and to uses of these antibodies in isolation of hematopoietic growth factors through affinity purification techniques, in assays for detection of hematopoietic growth factors and in immunological techniques for study of such growth factors. More specifically, the invention relates to monoclonal antibodies specifically reactive with human pluripotent granulocyte colony stimulating factor (hpG-CSF) from natural and recombinant sources.

The human blood-forming (hematopoietic) system replaces a variety of white blood cells (including neutrophils, macrophages, and basophils/mast cells), red blood cells (erythrocytes) and clot-forming cells (megakaryocytes/platelets). The hematopoietic system of the average human male has been estimated to produce on the order of $4.5 \times 10^{11}$ granulocytes and erythrocytes every year, which is equivalent to an annual replacement of total body weight. Dexter, et al., *BioEssays*, 2, 154–158 (1985).

It is believed that small amounts of certain hematopoietic growth factors account for the differentiation of a small number of progenitor "stem cells" into the variety of blood cell lines, for the tremendous proliferation of those lines, and for the ultimate differentiation of mature blood cells from those lines. Because the hematopoietic growth factors are present in extremely small amounts, the detection and identification of these factors has relied upon an array of assays which as yet only distinguish among the different factors on the basis of stimulative effects on cultured cells under artificial conditions. As a result, a large number of names have been coined to denote a much smaller number of factors. For example of the resultant confusion the terms, IL-3, BPA, multi-CSF, HCGF, MCGF and PSF are all acronyms which are now believed to apply to a single murine hematopoietic growth factor. Metcalf, *Science*, 229, 16–22 (1985).

The application of recombinant genetic techniques has brought some order out of this chaos. For example, the amino acid and DNA sequences for human erythropoietin, which stimulates the production of erythrocytes, have been obtained. (See, Lin, PCT Published Application No. 85/02610, published Jun. 20, 1985.) Recombinant methods have also been applied to the isolation of cDNA for a human granulocyte-macrophage colony-stimulating factor (GM-CSF) and human macrophage-specific colony-stimulating factor (CSF-1). [See, Lee, et al., *Proc. Natl. Acad. Sci. (USA)*, 82, 4360–4364 (1985); Wong, et al., *Science*, 228, 810–814 (1985) and Kowasaki, et al., *Science*, 230, 291–296 (1985).]

A human hematopoietic growth factor, called human pluripotent colony-stimulating factor (hpCSF) or pluripoietin, has been shown to be present in the culture medium of a human bladder carcinoma cell line denominated 5637 and deposited under restrictive conditions with the American Type Culture Collection, Rockville, Md. as A.T.C.C. Deposit No. HTB-9. The hpCSF purified from this cell line has been reported to stimulate proliferation and differentiation of pluripotent progenitor cells leading to the production of all major blood cell types in assays using human bone marrow progenitor cells. Welte, et al., *Proc. Natl. Acad. Sci. (USA)*, 82, 1526–1530 (1985).

Preliminary studies indicate that the factor identified as hpCSF has predominately granulocyte colony-stimulating activity during the first seven days in a human CFU-GM assay.

Another factor, designated human CSF-β has also been isolated from human bladder carcinoma cell line 5637 and has been described as a competitor of murine $^{125}$I-labelled granulocyte colony-stimulating factor (G-CSF) for binding to WEHI-3B D$^+$ cells in a dose-response relationship identical to that of unlabelled murine G-CSF [Nicola, et al., *Nature*, 314, 625–628 (1985)]. This dose-response relationship had previously been reported to be unique to unlabelled murine G-CSF and not possessed by such factors as M-CSF, GM-CSF, Il-3 [Nicola, et al., *Proc. Natl. Acad. Sci. (USA)*, 81, 3765–3769 (1984)]. See also, Metcalf, et al., *Leukemia Research*, Vol. 9, No. 5, pp. 521–527 (1985). CSF-β and G-CSF are also unique among CSF's in that they share a high degree of ability to induce differentiation of WEHI-3B D$^+$ cells. Nicola, et al., *Immunology Today*, 5, 76–80 (1984). At high concentrations, G-CSF stimulates mixed granulocyte-macrophage colony-forming cells [Nicola, et al., (1984) supra], which is consistent with preliminary results indicating the appearance of granulocytic, monocytic, mixed granulocytic/monocytic and eosinophilic colonies (CFU-GEMM) after 14 days incubation of human bone marrow cultures with hpCSF. CSF-β has also been described as stimulating formation of neutrophilic granulocytic colonies in assays which employed mouse bone marrow cells, a property which has been a criterion for identification of a factor as a G-CSF. On the basis of these similarities, human CSF-β has been identified with G-CSF (granulocytic colony stimulating factor). See, Nicola, et al., *Nature*, 314, 625–628 (1985).

Based upon their common properties, it appears that human CSF-β of Nicola, et al., supra, and the hpCSF of Welte, et al., supra, are the same factor which could properly be referred to as a human pluripotent granulocyte colony-stimulating factor (hpG-CSF).

Souza U.S. Pat. No. 4,810,643, hereby incorporated by reference, novel recombinant-produced polypeptides possessing part or all of the primary structural conformation and one or more of the biological properties of human pluripotent granulocyte colony stimulating factor are disclosed. Also disclosed are DNA sequences coding for such polypeptides, transformed host cells coding for such polypeptides and processes for the synthesis of such factors by recombinant methods.

Of interest to the background of the invention is current research focused on hybridoma techniques for producing tumor cell lines which will manufacture highly specific monoclonal antibodies to a selected antigenic substance. Techniques for the production of monoclonal antibodies are generally well known in the art. Typical descriptions of these procedures may be found in Wands, J. R., and Zurawski, V. R., Gastroenterology 80:225 (1981); Marshak-Rothstein, et al., J. Immunol. 122:2491 (1979); and Oi, V. T. and L. A. Herzenberg, "Immunoglobulin Producing Hybrid," Mishell, B. B. and S. M. Shiigi (eds.) *Selected Methods in Cellular Immunology,* San Francisco: W. H. Freeman Publishing, 1979 and Goding, "Antibody Production by Hybridomas" J. of Immunol. Meth. 39, 285–308 (1980). Briefly summarized, lymphocytes removed from the spleen of an animal previously injected with the antigen of interest are induced to fuse with myeloma cells in the presence of polyethylene glycol. Thousands of "hybrid" myeloma cells are produced from the fusion. The supernatant from growth of each "hybridoma" cell culture is tested for the presence of the desired antibody activity. When such activity is found in the supernatant of one cell culture, it is cloned by limiting dilutions, and the clones are individually assayed for supernatant activity.

Due to the highly specific nature of their immunological properties, monoclonal antibodies developed according to hybridoma techniques have been proposed for use as diagnostic reagents, therapeutic agents, and agents for affinity purification of specifically cross-reactive antigenic proteins from crude sources. See, e.g., *Trends in Biotechnology,* Vol. 3, No. 7 (July, 1985) and U.S. Pat. Nos. 4,465,624, 4,514,505 and 4,514,507.

While there exists a substantial need for specific monoclonal antibodies for use in detecting, isolating, purifying and studying hematopoietic growth factors such as human pluripotent granulocyte colony-stimulating factor, there have been no reports of the successful use of hybridoma techniques in obtaining monoclonal antibodies to hpG-CSF.

BRIEF SUMMARY

The present invention provides, for the first time hybridoma cell lines which produce monoclonal antibodies specifically immunoreactive with human pluripotent granulocyte colony-stimulating factor in an antigen/antibody reaction. Illustratively, the present invention provides new murine-derived hybridoma cell lines, A.T.C.C. HB-8957, A.T.C.C. HB-8958, A.T.C.C. HB-8959, A.T.C.C. HB-8960, A.T.C.C. HB-8961 and A.T.C.C. HB-8962, each of which produces, as a component of the supernatant of its growth in culture, a monoclonal antibody specifically reactive with hpG-CSF. Hybridoma cell lines, A.T.C.C. HB-8957, A.T.C.C. HB-8958, A.T.C.C. HB-8959, A.T.C.C. HB-8960, A.T.C.C. HB-8961 and A.T.C.C. HB-8962, are on deposit at the American type culture collection, 12301 Parklawn Drive, Rockville, Md. 20852.

According to the practice of the present invention, a hybrid tumor cell line is produced using a standard immunological technique as described in Oi and Herzenberg, "Immunoglobulin Producing Hybrid", supra and Goding, "Antibody Production by Hybridomas", J. of Immunol. Meth. 39 (1980) 285–308. Spleen cells from mice, hyperimmunized with natural hpG-CSF are fused with a mouse myeloma cell line in the presence of polyethylene glycol. The supernatant from growth of each "hybridoma" cell culture is tested for the presence of the desired antibody activity. A selected hybridoma cell is cloned to propagate a cell line which produces an antibody in its growth supernatant which has highly specific anti-hpG-CSF activity.

Monoclonal antibodies of the invention may be employed in immunological procedures for affinity purification and isolation of hpG-CSF (as well as other hematopoietic growth factors which may share common or related epitopes) from natural or recombinant sources. In such a procedure, a selected antibody would be immobilized (e.g., on a column) and the source material would be contacted with the immobilized antibody. hpG-CSF or antigenically related material would bind to the antibody and would thereafter be eluted from the immobilized antibody in a highly purified form. Antibodies of the invention may also be employed alone or jointly with each other or with polyclonal antibodies in immunological procedures (RIA's, ELISA's and the like) for the quantitative detection of hpG-CSF. Antibodies of the invention may also have utility in vivo to bind hpG-CSF or related factors in instances of overproduction of such factors. Other aspects of the present invention will become apparent upon consideration of the following detailed description.

DETAILED DESCRIPTION

The following examples illustrate practice of the invention in the production of a number of hybridoma cell lines including A.T.C.C. HB-8957, A.T.C.C. HB-8958, A.T.C.C. HB-8959, A.T.C.C. HB-8960, A.T.C.C. HB-8961 and A.T.C.C. HB-8962, the isolation of antibodies to hpG-CSF, and the amplification and characterization of the monoclonal antibodies.

More particularly, Example 1 is directed to stimulation of a murine host toward production of polyclonal serum antibodies to hpG-CSF, fusion of spleen cells with myeloma cells, and the screening, cloning and growth of hybridoma cells and isolation of monoclonal antibody therefrom. Example 2 relates to the characterization of the monoclonal antibodies so produced by ELISA and RIA assays, and competitive inhibition and neutralization assays as well as to the amplification of monoclonal antibody yields by the ascites method. Example 3 describes procedures for isolation and purification of hpG-CSF through the use of the monoclonal antibodies of the invention. Example 4 describes procedures for quantitative detection of hpG-CSF through the use of assay techniques utilizing antibodies of the invention.

EXAMPLE 1

A. Production of Polyclonal Serum

BALB/C mice each were injected with hpG-CSF purified by HPLC from human bladder carcinoma cell line No. 5637 (subclone 1A6) according to the procedures of Example 1(b) of Souza U.S. Pat. No. 4,810,643.

According to these procedures, cells of a bladder carcinoma cell line 5637 (subclone 1A6) as produced at Sloan-Kettering Institute, New York, N.Y. were obtained from Dr. E. Platzer. Cells were initially cultured Iscove's medium (GIBCO, Grand Island, N.Y.) in flasks to confluence. When confluent, the cultures were trypsinized and seeded into roller bottles (1½ flasks/bottle) each containing 25 ml of preconditioned Iscove's medium under 5% $CO_2$. The cells were grown overnight at 37° C. at 0.3 rpm.

Cytodex-1 beads (Pharmacia, Uppsala, Sweden) were washed and sterilized using the following procedures. Eight grams of beads were introduced into a bottle and 400 ml of PBS was added. Beads were suspended by swirling gently for 3 hours. After allowing the beads to settle, the PBS was drawn off, the beads were rinsed in PBS and fresh PBS was added. The beads were autoclaved for 15 minutes. Prior to use, the beads were washed in Iscove's medium plus 10% fetal calf serum (FCS) before adding fresh medium plus 10% FCS to obtain treated beads.

After removing all but 30 ml of the medium from each roller bottle, 30 ml of fresh medium plus 10% FCS and 40 ml of treated beads were added to the bottles. The bottles were gassed with 5% $CO_2$ and all bubbles were removed by suction. The bottles were placed in roller racks at 3 rpm for ½ hour before reducing the speed to 0.3 rpm. After 3 hours, an additional flask was trypsinized and added to each roller bottle containing beads.

At 40% to 50% of confluence the roller bottle cultures were washed with 50 ml PBS and rolled for 10 min. before removing the PBS. The cells were cultured for 48 hours in medium A [Iscove's medium containing 0.2% FCS, $10^{-8}$M hydrocortisone, 2 mM glutamine, 100 units/ml penicillin, and 100 μg/ml streptomycin]. Next, the culture supernatant was harvested by centrifugation at 3000 rpm for 15 min., and stored at −70° C. The cultures were refed with medium A containing 10% FCS and were cultured for 48 hours. After discarding the medium, the cells were washed with PBS as above and cultured for 48 hours in medium A. The supernatant was again harvested and treated as previously described.

Approximately 30 liters of medium conditioned by 1A6 cells were concentrated to about 2 liters on a Millipore Pellicon unit equipped with 2 cassettes having 10,000 M.W. cutoffs at a filtrate rate of about 200 ml/min. and at a retentate rate of about 1000 ml/min. The concentrate was diafiltered with about 10 liters of 50 mM Tris (pH 7.8) using the same apparatus and some flow rates. The diafiltered concentrate was loaded at 40 ml/min. onto a 1 liter DE cellulose column equilibrated in 50 mM Tris (pH 7.8). After loading, the column was washed at the same rate with 1 liter of 50 mM Tris (pH 7.8) and then with 2 liters of 50 mM Tris (pH 7.8) with 50 mM NaCl. The column was then sequentially eluted with six 1 liter solutions of 50 mM Tris (pH 7.5) containing the following concentrations of NaCl: 75 mM; 100 mM; 125 mM; 150 mM; 100 mM; and 300 mM. Fractions (50 ml) were collected, and active fractions were pooled and concentrated to 65 ml on an Amicon ultrafiltration stirred cell unit equipped with a YM5 membrane. This concentrate was loaded onto a 2 liter AcA54 gel filtration column equilibrated in PBS. The column was run at 80 ml/hr. and 10 ml fractions were collected. Active fractions were pooled and loaded directly onto a C4 high performance liquid chromatography (HPLC) column.

Samples, ranging in volume from 125 ml to 850 ml and containing 1–8 mg of protein, about 10% of which was hpG-CSF were loaded onto the column at a flow rate ranging from 1 ml to 4 ml per minute. After loading and an initial washing with 0.1M ammonium acetate (pH 6.0–7.0) in 80% 2-propanol at a flow rate of 1/ml/min. One milliliter fractions were collected and monitored for proteins at 220 nm, 260 nm and 280 nm.

As a result of purification, fractions containing hpG-CSF were clearly separated (as fractions 72 and 73 of 80) from other protein-containing fractions. The material was purified with a C4 HPLC column to in excess of 85% purity and had a concentration of approximately 60 μg/ml in a solution comprising 50% propanol and 100 mM ammonium acetate (pH 7). Each of 10 mice was initially given multiple subcutaneous injections totalling approximately 0.1 ml of an inoculant (7.2 μg hpG-CSF per mouse) comprising 1.2 ml of the hpG-CSF solution which had been concentrated to 0.6 ml by speed vacuuming and then mixed by sonication with 0.6 ml of BACTO-Freund's complete adjuvant H37 Ra (DIFCO 3113–60). Eighteen days later the mice were each given multiple subcutaneous booster injections totalling approximately 0.15 ml of an inoculant (7.2 μg hpG-CSF per mouse) comprising 1.2 ml of the hpG-CSF solution concentrated to 0.75 ml and mixed with 0.75 ml of Freund's incomplete adjuvant (BACTO 0639-60-6 from DIFCO).

Four days later the mice were bled and their sera screened by RIA for production of anti-hpG-CSF antibodies. hpG-CSF used in the serum assay comprised approximately 0.5 ml of 80% pure hpG-CSF at a concentration of approximately 100 μg/ml in a solution comprising 100mM ammonium sulfate and 50% propanol which had been concentrated four times. Two hundred and fifty μl of the above solution was concentrated to 150 μl and was mixed with 5 ml of 50 mM $CO_3^{-2}$/$HCO_3^{-1}$ buffer (pH 9.2). Fifty μl of this material was then applied to each well in a 96 well tray and incubated for 2 hours at room temperature and overnight at 4° C. A blocking compound comprising 5% bovine serum albumin (BSA) was incubated for thirty minutes in the wells. Test serum diluted at ratios of 1:5, 1:25, 1:625, and 1:3125 and control (non-inoculated) serum diluted at ratios of 1:5 and 1:125 was applied to the wells at 50 μper well and incubated for two hours at room temperature. The wells were then washed three times using Wash Solution [(Kirkeguard & Perry Laboratories, (KPL) Gaithersburg, Md.)]. Rabbit anti-mouse IgG antibody labeled with $^{125}I$ was then applied such that it produced approximately 199,000 counts per minute per 50 μl well and incubated for 1.5 hours at room temperature. The wells were then washed five times with Wash Solution and their radioactivity was determined with a gamma counter.

Twenty-one days after the booster injection, five mice detected by the RIA to be producing anti-hpG-CSF antibodies were given a third injection. The mice were immunized with the same material as during their booster injection but were given approximately 10 μg hpG-CSF per mouse.

B. Cell Fusion

In the hybridoma production procedure the spleens of the inoculated mice are disrupted to suspend anti-hpG-CSF antibody producing lymphocytes. These spleen cells are fused with cells from an SP2/0 myeloma cell line to form hybrid cells. The cell membranes of spleen and myeloma cells fuse and initially surround a common cytoplasm with two or more nuclei. Several days after fusion of the cell membranes, the nuclei fuse and become capable of synchronous mitosis. As these fused cells divide, a variable number of chromosomes of both fused partners are lost until the hybrid cell lines stabilize. A hypoxanthine aminopterin-thymidine (HAT) media prevents SP2/0:SP2/0 hybrids produced during the hybridization procedure or unfused SP2/0 cells from growing while spleen:spleen cell hybrids or unfused spleen cells will generally die after two weeks in culture. Thus only the SP2/0:spleen hybrid cells will survive in the cultures.

Three days after the second booster inoculation the mice were sacrificed by cervical dislocation and doused with 70% ethanol. Spleens of the mice were removed aseptically and placed in a sterile petri dish on ice containing DMEM (Dulbecco's Modified Eagle's Medium, Catalogue No. 320-1885, lot 18K3252 from GIBCO) supplemented with penicillin G-streptomycin solution (a "1X" solution), hereinafter "1XPS" solution, (catalogue no. 9366 from Irvine Scientific) comprising 100 units of penicillin G and 100 mcg of streptomycin per ml. Fatty tissue adhering to the spleens was removed and the spleens were washed twice with DMEM containing 2XPS (200 units penicillin G and 200 mcg streptomycin per ml) and placed in a sterile stomacher bag on ice. To the bag was added solution comprising DMEM—2XPS. The spleens were disrupted in a stomacher apparatus and then filtered through four layers of sterile gauze into 50 ml centrifuge tubes. The bag and filters were washed with up to 40 ml of solution comprising DMEM—2XPS solution. The cells were then centrifuged for ten minutes at 1000 rpm in a IEC NH-SII centrifuge (Damon/IEC Division) and the supernatant was gently aspirated. The cells were then washed twice with a solution comprising DMEM—2XPS and once with DMEM with no additives. The cells were then resuspended in DMEM.

Myeloma cells (Sp2/0) were grown in HB101 medium containing 1XPS and 1% Fetal Bovine Serum (FBS) (Irvine Scientific Catalogue No. 3000, Lot No. 209608, Heat inactivated) and were expanded in log growth phase for 3 days. The SP2/0 cells were harvested by pelleting in an IEC NH-SII centrifuge at 1000 rpm for ten minutes. The cells were washed in DMEM solution and then suspended in DMEM solution.

The spleen cells were then combined with the myeloma cells in a 50 ml centrifuge tube at a ratio of 4:1 and centrifuged for ten minutes at 1000 rpm and the supernatant aspirated. The pellet was then placed in a 37° C. water bath under a hood. Polyethylene glycol (1500 molecular weight, M. A. Bioproducts, catalogue number 17- 780Z, lot number 4J030) was melted and then mixed at a one to one ratio by volume with DMEM solution to make a 50% solution. The PEG solution was then added to the cells according to the following procedure. During the first minute, 1.0 ml of the 50% PEG solution was added. During the second minute, the solution was stirred gently using a pipette which was stirred constantly with a circular motion but which avoided touching the sides or bottom of the tubes. During the third minute, 1.0 ml of solution comprising DMEM, 10% FCS and 1XPS was added. During the fourth minute, 1.0 ml of the same solution was again added. During the fifth and sixth minutes, 8.0 ml of the same solution was again added. The mixture was then centrifuged at 1000 rpm for 10 minutes on the IEC NH-SII centrifuge. Supernate in centrifuge tube was aspirated and the cells were gently resuspended in 100 to 150 ml of media comprising DMEM with 10% FBS and 1XPS. The cell suspension was then plated at a rate of 0.1 ml of suspension per well onto approximately 800 wells on eight and one half 96 well plates which had been pre-equilibrated in a $CO_2$ incubator. The plates were then returned to a $CO_2$ incubator with an approximate 7% $CO_2$ content at 37° C.

One day later, 100 µl of HAT medium in DMEM and 10% FBS was added to each well. On the second day, 100 µl of spent medium was aspirated from each well and replaced with 100 µl of fresh HAT medium in DMEM with 10% FBS. This procedure was repeated on day 2, day 4, day 7 and day 11. On day 14, 100 µl of spent medium was removed from each well and replaced with 100 µl of HT medium comprising 1.36 mg/dl of hypoxanthine and 0.76 mg/dl of thymidine. The procedure was repeated on day 18, day 22 and day 26. On day 28, the cultures were fed with a complete medium comprising DMEM with 10% FBS. The cultures were subsequently re-fed twice a week with this complete medium. On day 17 the wells were screened for production of immunoglobulin utilizing antimouse IgG antibodies. RIA and ELISA assays showed that approximately 260 out of 800 wells were significantly positive for mouse IgG.

EXAMPLE 2

Initial Characterization of Monoclonal Antibodies

An ELISA assay was conducted for the detection of those clones which were producing anti-hpG-CSF antibodies. Wells of 96 well trays were coated by applying approximately 50 µl of solution containing 100 ng of 90% pure hpG-CSF was diluted in 50 mM $CO_3^{-2}/HCO_3^-$ buffersolution (pH 9.2) at room temperature for two hours then added to each well of the trays and was incubated overnight at 4° C. The wells were then treated with a 5% BSA blocking solution which was incubated for 30 minutes.

Supernatant from the hybridoma cultures was diluted in PBS solution (pH 7.0) containing 1% BSA and was then incubated against the coated wells for 2 hours at room temperature. The wells were then washed three times with Wash Solution and were treated with horseradish peroxidase labeled anti-mouse IgG antibody (BMB No. 605-250) at a 1:300 dilution for 1.5 hours. The wells were then washed five times with Wash Solution and peroxidase substrate ABTS (KPL) was added at a rate of 50 µl per well. The wells were then read for optical density at 414 nm by a Titertek Multiscan (Flow Labs, McLean, Va.) spectrophotometer. Twenty-three of the wells (Nos. 3, 4, 5, 20, 21, 28, 35, 37, 39, 40, 58, 61, 63, 64, 66, 68, 72, 74, 75, 98, 151, 182 and 231) were found to significantly react with the reduced hpG-CSF.

Formal cloning of hybridoma cells obtained from the positive wells was conducted by diluting the cells into additional wells at a ratio such that there was approximately 1 cell per 3 wells. Generally, formal cloning from an active well produced formal clones which appeared to be subclones of the same hybridoma cell but in several instances revealed different clone populations exhibiting different antibody subtypes and reaction properties. Subclones from the same well were labeled with a letter (e.g., clones obtained from well 4 were labeled 4A, 4B, etc.).

An ELISA assay was conducted to determine reactivity of the monoclonal antibodies against natural hpG-CSF as well as reduced natural hpG-CSF. Supernatant obtained from wells found to be producing antibodies reactive with hpG-CSF was tested against both natural hpG-CSF and natural hpG-CSF which had been denatured with SDS/mercaptoethanol. Antibodies from the clones reacted against both materials with approximately equal specificity suggesting that the antibodies may be specifically reactive with antigenic epitopes primarily determined by continuous sequences of amino acids (the primary structure) of the protein.

B. Reactivity of Monoclonal Antibodies Against Mammalian and Recombinant hpG-CSF In this example, solid phase RIA and ELISA assays to measure reactivity of hybridoma supernatant obtained from the active wells were conducted on mammalian hpG-CSF as well as recombinant *E. coli* produced hpG-CSF. In all but one case, monoclonal antibody material which reacted with mammalian produced (natural) hpG-CSF reacted equally well with recombinant produced hpG-CSF. That case involved subclones 35B, 35D and 35I which produced antibodies which were significantly less reactive with the recombinant material than with the mammalian derived material in direct binding assays.

C. Screening for Antibody Subtypes

In this example, formal clones obtained from the 23 wells found to be active originally were screened by RIA for determination of their antibody subtype. Ninety-six well trays were treated with rabbit anti-mouse-immunoglobulin antibodies of differing subtype specificities. The anti-mouse-immunoglobulin antibodies included rabbit anti-mouse $IgG_1$ (MILES Laboratories, Naperville, Ill., 64-360-1), rabbit anti-mouse $IgG_{2a}$ (MILES, 64-361-1), rabbit anti-mouse $IgG_{2b}$ (MILES, 64-362-1), rabbit anti-mouse $IgG_3$ (MILES, 64-363-1), rabbit anti-mouse IgM (MILES, 64-365-1) and rabbit anti-mouse IgG (MILES, 65-157-2). Each well was coated with 50 µl of the anti-mouse-immunoglobulin antibody solution in a $CO_3^{-2}/HCO_3^{-}$ (pH 9.6) buffer solution comprising approximately 0.5 µg of antibody and was incubated for 2 hours at room temperature and overnight at 4° C. The wells were then blocked by incubation with a 5% BSA solution for 30 minutes. Each well was then incubated with hybridoma tissue culture supernatant for 2 hours at room temperature and washed three times with Wash Solution. The wells which had been treated with anti-IgG antibody were then incubated for 1.5 hours with 50 µl per well of $^{125}I$ rabbit anti-mouse-IgG antibody while the wells which had been treated with anti-IgM were then incubated for 1.5 hours with 50 µl per well of $^{125}I$ rabbit anti-mouse-IgM antibody. The wells were then washed five times with Wash Solution and were counted in a gamma counter. The results of analysis of the original 23 clones indicates that 2 wells (Nos. 37 and 182) stopped synthesis of IgG; 1 well was indicated IgG positive but did not demonstrate reactivity in early screening to hpG-CSF (No. 58); 15 wells showed positive for $IgG_1$ (Nos. 4C, 5, 28, 39, 40, 61, 63, 64, 66, 68, 72, 74, 75, 98 and 231). A subclone of one of these, No. 5d was found to be reactive with both anti-$IgG_3$ and anti-IgM antibodies. Four wells were positive for $IgG_{2a}$ production (Nos. 3, 4A, 21 and 151) and 1 well for $IgG_{2b}$ production (No. 35).

D. Neutralization of hpG-CSF Activity as Measured by $^3H$-Thymidine Uptake

In this example, monoclonal antibodies raised against hpG-CSF were tested for the ability to neutralize the biological activity of hpG-CSF of stimulating the incorporation of $^3H$-thymidine into human bone marrow cells. In order to test for neutralization of $^3H$-thymidine uptake, recombinant or natural hpG-CSF was incubated with various concentrations of antibodies according to the invention at 4° C. for 12 hours. The solutions were then added to low density, non-adherent human bone marrow cells and processed according to methods described in Example 7 of copending U.S. patent application Ser. No. 768,959. Antibodies from clone nos. 20A, 35B, 39B, 40A, 61D, 63D, 75A and 151K, among others, were tested with antibodies from clone no. 75A being the most effective in neutralizing the effect of the hpG-CSF on $^3H$-thymidine uptake and with all of the above antibodies demonstrating various degrees of neutralizing, effect on $^3H$-thymidine uptake with the exception of antibodies produced by clone no. 35B.

E. Neutralization of hpG-CSF Activity as Measured by Cell Differentiation Induction In this example antibodies raised against hpG-CSF were tested for the ability to neutralize the ability of hpG-CSF to induce differentiation of the murine myelomonocytic leukemic cell line WEHI-3B $D^+$. Various concentrations of the antibodies produced according to the invention (from clones nos. 20A, 39B, 40A, 61D, 63D and 75A) were incubated with hpG-CSF at 4° C. for 12 hours. The solutions were then added to WEHI-3B $D^+$ cells in an agar suspension according to the method described in Example 7 of copending U.S. patent application Ser. No. 768,959. Antibodies produced by clone nos. 40A, 61D and 75A showed the ability to block differentiation. Because these monoclonal antibodies have different precipitating abilities toward hpG-CSF the fact that some block the differentiation inducing ability of hpG-CSF while others do not cannot be explained simply on the basis of strength of affinity. Significantly, monoclonal antibody produced by clone 75A not only inhibited differentiation of the WEHI-3B D+ cells but also inhibited cell growth suggesting that it may cross-react with a murine growth factor secreted by WEHI-3B D+ cells and may have antiproliferative effects independently of its capacity to bind hpG-CSF.

F. Eptiope Characterization

In this example, competitive binding studies were conducted utilizing $^{125}I$ labeled antibody from clones 75A and 151K and immobilized recombinant produced hpG-CSF. In these studies, antibodies from other clones were allowed to compete against 75A and 151K radio-labelled monoclonal antibodies bound to recombinant produced hpG-CSF. After incubation and washing according to procedures well known in the art, radiation counts were taken to determine the extent to which either 75A produced antibody or 151K-produced antibody had been displaced from the hpG-CSF.

Results from these assays indicate that antibodies produced by clones nos. 63D, 75A, and 151K may share overlapping portions of a common antigenic epitope on the hpG-CSF protein. The results also indicate that antibodies produced by clone nos. 4C, 28A, and 35B appear reactive with an epitope or epitopes of the hpG-CSF protein for which the 75A and 151K produced antibodies are not specifically reactive. The results also suggest that the hpG-CSF binding properties of antibodies produced by clones 40A and 61D may be distinguishable from those of antibodies produced by clones 4C, 28A, 35B, 75A and 151K.

Properties of Antibodies from Deposited Representative Cell Lines

Representative novel hybridoma cell lines capable of producing monoclonal antibodies representative of those provided by the present invention have been deposited with the American Type Culture Collection, 12301 Parklawn Drive, Rockville, Md. 20852. These cell lines correspond to cell lines developed during the formal cloning procedure as follows: clone 4C (A.T.C.C. HB-8962), Clone 28A (A.T.C.C. HB-8957), clone 35B (A.T.C.C. HB-8960), clone 63D (A.T.C.C. HB-8958), clone 75A (A.T.C.C. HB-8959) and clone 151K (A.T.C.C. HB-8961). The properties of antibodies produced by these clones are summarized in table 1 below.

TABLE 1

| | | Binding | | Neutralization | | Epitope Characterization Similarity | |
|---|---|---|---|---|---|---|---|
| Clone No. | Type | E. coli | Native | $^3$H-Thy (Human BM) | WEHI 38 D$^{+3}$ | 75A | 151K |
| 4C | IgG$_1$ | + | + | ND | ND | – | – |
| 28A | IgG$_1$ | + | + | ND | ND | – | – |
| 35B | IgG$_{2b}$ | ± | + | – | ND | – | – |
| 63D | IgG$_1$ | + | + | ± | – | + | + |
| 75A | IgG$_1$ | + | + | +++ | + | + | + |
| 151K | IgG$_{2a}$ | + | + | ++ | ND | + | + |

ND (experiment not done)

H. Amplification of Antibody Yields by Ascites Method

To obtain a more concentrated antibody than that produced in tissue culture, the monoclonal antibodies of the present invention were amplified by the ascites method generally described in Kenneth, et al. (eds.), *Monoclonal Antibodies, Hybridomas: A New Dimension in Biological Analysis*, p. 403, New York: Plenum Press (1981). According to this procedure, mice are primed with 0.5 ml of Pristane (2,6,19,14-tetra methylpentadecane, obtained from Aldrich Chemical Co.) injected into their peritoneal cavities by means of 25 or 27 gauge needles. Pristane treatment permits the growth of tumor cells in an ascitic form within the peritoneal cavity. After approximately 1–2 weeks, approximately 10$^6$ hybridoma cells are injected into the peritoneal cavities of the mice in serum-free Dulbecco's modified eagles medium (DMEM) (Irvine Scientific Co.) or HB101 (Hanna Biologicals, Berkeley, Calif.). The set of injections is performed on mice for each of the clones.

Approximately 1–3 weeks after the injection of the hybridoma cells, ascites fluid was obtained from the intraperitoneal cavities of the mice by making small cuts into the skin and pipetting out the fluid. Ascitic fluid was clarified by centrifugation and then frozen. Ascites fluid antibodies can be further purified from ascites fluid albumin by precipitation with 45% ammonium sulfate and protein A-sepharose chromatography.

EXAMPLE 3

Isolation and Purification of Hematopoietic Growth Factors

Through its provision of highly specific and highly reactive anti-hpG-CSF monoclonal antibodies, the present invention makes possible for the first time the isolation of hpG-CSF and hematopoietic growth factors from fermentation cultures as well as from natural mammalian sources according to affinity purification procedures well known in the art. Briefly put, preferred isolation procedures would involve immobilizing an antibody of the invention on a solid support (e.g., a chromatographic column), contacting the hpG-CSF or hematopoietic factor-containing fluid with the immobilized antibody and thereafter eluting purified hpG-CSF or hematopoietic growth factor from immune complex association with the antibody. By adjusting the particular antibody used, the purification technique may allow the isolation of native hpG-CSF in its correctly folded conformation from incorrectly folded or denatured hpG-CSF. Analogues of hpG-CSF could be isolated and studied as could specific antigenic epitopes of hematopoietic growth factor molecules.

EXAMPLE 4

Quantitative Detection of Hematopoietic Growth Factors

Through its provision of highly specific anti-hpG-CSF monoclonal antibodies, the present invention also makes possible novel solid or liquid phase assays for quantitative detection of hpG-CSF and hematopoietic growth factors in a fluid sample which employ more than one antibody. Solid phase assays would typically include the steps of:

(1) contacting the fluid with a first, immobilized, antibody which reacts with a first antigenic determinant of hpG-CSF in the fluid to form an immunological complex of hpG-CSF and the first antibody; (2) contacting the complex formed in step (1) with a second antibody which reacts with an antigenic determinant of hpG-CSF other than the first antigenic determinant, to form an immunological complex of hpG-CSF and the second antibody; and (3) quantifying the amount of the second antibody bound to the immunological complex formed in step (2).

Liquid phase competition assays would involve labelling of hpG-CSF and precipitation of the same with one or more antibodies of the invention. Quantitation of unlabled hpG-CSF or related factors could then be accomplished in a competitive binding format. Such assay procedures would preferably include two of the above described monoclonal antibodies, but may also be developed using one of the monoclonal antibodies and a polyclonal serum derived antibody to hpG-CSF.

Numerous modifications and variation in practice of the invention are expected to occur to those skilled in the art upon consideration of the foregoing descriptions of preferred embodiments thereof. Consequently, only such limitations should be placed on the invention as appear in the following claims.

What is claimed is:

1. A murine-derived hybridoma cell line capable of producing in the medium of its growth a monoclonal antibody capable of specifically binding with hpG-CSF in an antigen/antibody reaction, wherein the cell line is selected from the group consisting of A.T.C.C. HB-8957, HB-8958, HB-8959, HB-8960, HB-8961 and HB-8962.

2. A monoclonal antibody produced by a cell line capable of producing in the medium of its growth a monoclonal antibody capable of specifically binding with hpG-CSF in an antigen/antibody reaction, wherein the cell line is selected from the group consisting of A.T.C.C. HB-8957, HB-8958, HB-8959, HB-8960, HB-8961 and HB-8962.

3. In an immunological procedure for the isolation of biologically active hpG-CSF from a biological fluid on the basis of a selective immunological reaction with an antibody specific for hpG-CSF, the improvement comprising:

employing a monoclonal antibody capable of specifically binding hpG-CSF in an antigen/antibody reaction, wherein the monoclonal antibody is produced by a cell line selected from the group consisting of A.T.C.C. HB-8957, HB-8958, HB-8959, HB-8960, HB-8961 and HB-8962.

4. In an immunological procedure for the quantitative detection of hpG-CSF in a biological fluid on the basis of one or more selective immunological reactions with an antibody specific for hpG-CSF, the improvement comprising:

employing one or more monoclonal antibodies capable of specifically binding with hpG-CSF in an antigen-antibody reaction, wherein the monoclonal antibody is produced by a cell line selected from the group consisting of A.T.C.C. HB-8957, HB-8958, HB-8959, HB-8960, HB-8961 and HB-8962.

* * * * *